United States Patent [19]

Yearn et al.

[11] Patent Number: 5,356,951
[45] Date of Patent: Oct. 18, 1994

[54] COMPOSITION FOR DENTAL RESTORATIVE MATERIAL

[75] Inventors: John A. Yearn, Palos Heights, Ill.; Tetsuro Sakuma, Tokorozawa, Japan

[73] Assignee: GC Corporation, Tokyo, Japan

[21] Appl. No.: 995,825

[22] Filed: Dec. 23, 1992

[30] Foreign Application Priority Data

Jan. 13, 1992 [JP] Japan ................... 4-021660

[51] Int. Cl.$^5$ ............................ A61K 6/08; C08J 3/20
[52] U.S. Cl. ..................... 523/116; 523/115; 523/117
[58] Field of Search ............ 523/115, 116, 117; 524/436

[56] References Cited

U.S. PATENT DOCUMENTS

| | | | |
|---|---|---|---|
| 4,388,069 | 6/1983 | Orlowski | 523/116 |
| 4,649,165 | 3/1987 | Kuhlman | 523/117 |

*Primary Examiner*—Paul R. Michl
*Assistant Examiner*—LaVonda DeWitt
*Attorney, Agent, or Firm*—Oblon, Spivak, McClelland, Maier & Neustadt

[57] ABSTRACT

A composition for dental restorative material comprises a methacrylate or acrylate monomer, a specific organic-/inorganic composite filler, a specific glass powder component having a specific particle diameter, a fine-particle filler having a specific particle diameter and a photopolymerization initiator, this composition being as excellent in surface smoothness as natural teeth, is less shrinkable by polymerization so that no gap can occur between the restorative material and the tooth having roentgenographic properties.

10 Claims, No Drawings

COMPOSITION FOR DENTAL RESTORATIVE MATERIAL

BACKGROUND OF THE INVENTION

1. Field of the Invention

The present invention relates to a composition for dental restorative material and, more specifically, to a dental composition which is as excellent in surface smoothness as natural teeth, and less shrinkable by polymerization so that no gap can occur between the tooth and the restorative material, having excellent physical properties and being improved in terms of roentgenographic properties.

2. Prior Art

The filler used so far for dental composite resin restorative material is glass powders having a maximum particle diameter of 10 to 50μm. However, the composite resin incorporating such a large particle-diameter filler fails clinically to give any smoothly finished surface comparable to natural teeth. Now, many makers present dental composite in which fillers resins fine-particle (hereinafter referred to as the fine fillers) having a mean particle diameter of 0.01 to 0.04 μm only are incorporated to obtain surface smoothness.

However, these fine particle fillers have a large specific surface area and give rise in an increase in the amount of the monomers in the composite resins; that is, their proportion in the composite resins is as small as 30 to 60% by weight, making the physical properties likely to deteriorate, e.g., the shrinkage by polymerization likely to become large. There is also commercially available a certain type of composite resins which, as means for making up for this shrinkage by polymerization, uses an organic/inorganic composite filler obtained by mixing the monomer with a fine filler having a mean particle diameter of 0.01 to 0.04μm, and curing and pulverizing the mixture. The organic/inorganic composite filler, because of having a small specific surface area, enables the amount of the monomer to be reduced, serves well to make up for the shrinkage by polymerization, and has surface smoothness as well. However, since the fine filler having a mean particle diameter of 0.01 to 0.04 μm is used in the organic/inorganic composite filler, the content of the inorganic material in the cured product is very low. This in turn causes an increase in the coefficient of thermal expansion, which is otherwise responsible for lack of border seal in the mouth. In general, colloidal silica is used as the fine filler of the organic/inorganic composite filler, but this has a serious demerit of being lacking in the radioopacity that conservation material is required to have. Currently, restorative material using glass powders having a mean particle diameter of 2 μm is mainly used and put on the market in the West. This restorative material has clinically sufficient surface smoothness. Still, this contains large amounts of monomer components and so poses a grave problem in connection with the shrinkage by polymerization.

We have made intensive and extensive studies as to a composition for dental restorative material which is as excellent in surface smoothness as natural teeth, is less shrinkable by polymerization so that no gap can be presented between the tooth and the restorative material, has excellent physical properties and is improved in terms of roentgenographic properties, and have achieved the present invention by finding that the object mentioned above is attained by the provision of a composition for dental restorative materials which comprises a novel combination of an organic/inorganic composite filler, a glass powder component and a fine filler.

We have also found that clinically sufficient surface smoothness is obtained by using a glass powder component having a maximum particle diameter of 10 μm or less and a mean particle diameter of 0.1 to 5 μm as a filler having roentgenographic properties. Additionally, we have found that if the roentgenographic glass powder component has such a particle diameter, then the glass powder component accounts for 60% or more by weight of the organic/inorganic composite filler, and that the combination of the glass powder component with the organic/inorganic composite filler provides a restorative material which has a reduced coefficient of thermal expansion, is less shrinkable by polymerization and is improved in terms of physical properties as well. The incorporation of the transparent, roentgenographic glass powder component in the filler achieves clinically sufficient roentgenographic properties and imparts sufficient transparency to the restorative material.

SUMMARY OF THE INVENTIVE

More specifically, this invention provides a composition for dental restorative material comprising:

(a) a methacrylate or acrylate monomer having at least one unsaturated double bond, (b) (i) an organic/inorganic composite filler obtained by curing and pulverizing a mixture of glass powders having a maximum particle diameter of 10 μm or less and a mean particle diameter of 0.1 to 5 μm with a methacrylate or acrylate monomer having at least one unsaturated double bond, (ii) a glass powder component having a maximum particle diameter of 10 μm or less and a mean particle diameter of 0.1 to 5 μm, and (iii) a fine filler having a mean particle diameter of 0.01 to 0.04 μm, and (c) a photopolymerization initiator.

DETAILED EXPLANATION OF THE INVENTION

In the ensuing description, the present invention will be explained at great length.

Referring specifically to the methacrylate or acrylate monomer having at least one unsaturated double bond, use may be made of methyl methacrylate, ethyl methacrylate, isopropylmethacrylate, 2-hydroxyethyl methacrylate, n-butyl methacrylate, isobutyl methacrylate, 3-hydroxypropyl methacrylate, tetrahydrofurfuryl methacrylate, glycidyl methacrylate, 2-methoxyethyl methacrylate, 2-ethylhexyl methacrylate, benzyl methacrylate, 2,2-bis(methacryloxyphenyl)propane, 2,2-bis[4-(2-hydroxy-3-methacryloxypropoxy)phenyl]propane, 2,2-bis(4-methacryloxypolyethoxylphenyl)propane, ethylene glycol dimethacrylate, diethylene glycol dimethacrylate, triethylene glycol dimethacrylate, butylene glycol dimethacrylate, neopentyl glycol dimethacrylate, 1,3-butanediol dimethacrylate, 1,4-butanediol dimethacrylate, 1,6-hexanediol dimethacrylate, trimethylolpropane trimethacrylate, trimethylolethane trimethacrylate, pentaerythritol trimethacrylate, trimethylolmethane trimethacrylate and pentaerythritol tetramethacrylate or these acrylates. Use may also be made of methacrylates and acrylates having urethane bonds in their molecules. Particularly mentioned are di-2-methacryloxyethyl-2,2,4-trimethylhexamethylene dicarbamate and its acrylate, or one represented by the following structural formula (1):

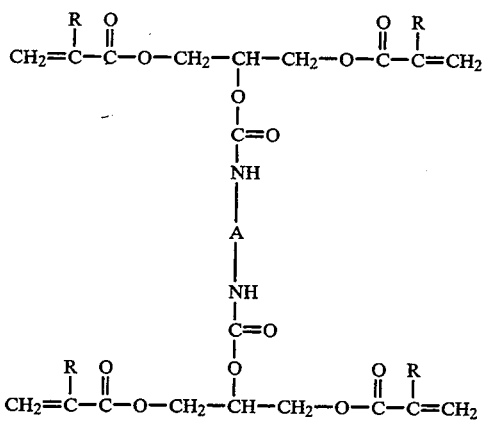

where Rs, which may be identical with or different from each other, stand for H or CH$_3$, and —(A)— denotes —(CH$_2$)$_6$—.

Methacrylates or acrylates represented by the following formulae (2) and (3):

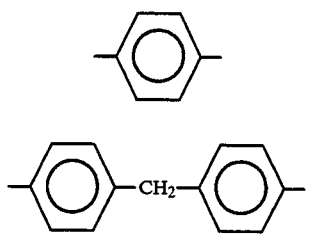

are also preferable. These methacrylate or acrylate monomers are known as dental material, and so may be used alone or in admixture, if required. The proportion of the monomer lies in the range of 5 to 30% by weight based on the total weight of the present composition for dental restorative material.

The component (b-i) of the present composition used is an organic/inorganic composite filler obtained by curing and pulverizing a mixture of glass powders having a maximum particle diameter of 10 μm or less and a mean particle diameter of 0.1 to 5 μm with a methacrylate or acrylate monomer having at least one unsaturated double bond.

To this end any desired glass powders may be used. Specific and particular roentgenographic glass used in this invnetion, for instance, may be glass containing alkaline earth metals such as calcium, strontium and barium, zinc glass and lead glass. The amount of the roentgenographic glass used may be such that radiograms can be clinically observed, but should preferably lie in the range of 20% or more by weight based on the total weight of the glass powders incorporated in the present composition for dental restorative material. If the glass powders have a maximum particle diameter of 10 μm or less and a mean particle diameter of 0.1 to 5 μm, the final restorative material is satisfied in terms of surface smoothness. More preferably, the glass powders used have a maximum particle diameter of 5 μm or less and a mean particle diameter of 0.1 to 2 μm. The amount of the glass powders used should preferably account for 60 to 90% by weight of the organic/inorganic composite filler.

As the methacrylate or acrylate monomer having at least one unsaturated double bond used for the organic-/inorganic composite filler, use may be made of the same methacrylate or acrylate monomer having at least one unsaturated double bond as mentioned in connect ion with (a). It is preferred that the same monomer as (a) be used, because the final restorative material is well improved in terms of transparency.

These glass powders and monomers are mixed together by means of a mixer, followed by curing and pulverization. For the purpose of curing, a curing agent has been pre-dissolved in the monomer; an organic peroxide or azo compound may be used for thermal curing. For photo-setting, a photopolymerization initiator or the like has been pre-dissolved in the monomer. Besides, chemical polymerization or other procedures may be conceived, and no critical limitation is placed on how to polymerize the monomer in this invention.

It is preferred that the is thus obtained organic/inorganic composite filler have a mean particle diameter of 5 to 50 μm, and be used in an amount of 20 to 80% by weight on the basis of the total weight of the present composition for dental restorative material. As the glass powder component (b-ii) having a maximum particle diameter of 10 μm or less and a mean particle diameter of 0.1 to 5 μm, use should preferably be made of the same glass powders as used in the organic/inorganic composite filler (b-i) in a quantity of 5 to 60% by weight on the basis of the total weight of the present composition for dental restorative material.

As the fine filler (b-iii) having a mean particle diameter of 0.01 to 0.04 μm, generally available colloidal silica may be used in an amount of 1 to 8% by weight on the basis of the total weight of the composition for dental restorative material so as to prevent any undesired liquid separation.

As the photopolymerization initiator (c), use may generally be made of combinations of sensitizers with reducers. The sensitizers used, for instance, include camphor quinone, benzil, diacetyl, benzyl diethyl ketal, benzyldiethyl ketal, benzyl-di(2-methoxyethyl)ketal, 4,4'-dimethylbenzyl-dimethylketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diethylthioxanthone, 2,4-diisopropylthioxanthone, 2-chloro-7-trifluoromethylthioxanthone, thioxanthone-10,10-dioxide, thioxanthone-10-oxide, benzoin methyl ether, benzoin ethyl ether, benzoin isopropyl ether, benzoin isobutyl ether, benzophenone, bis(4-dimethylamylphenyl)ketone, 4,4'-bis-diethylaminobenzo-phenone and azide-containing compounds. These may be used alone or in admixture.

As the reducing agents use may generally be made of tertiary amines. The tertiary amines used, for instance or preferably, include dimethylaminoethyl methacrylate, triethanolamine, 4-dimethylamino benzoic acid methyl, 4-dimethylaminobenzoic acid ethyl and 4-dimethylaminobenzoic acid isoamyl. Other reducers may be used as well, including benzoyl peroxide, organic metal compounds and sulfinic acid derivatives. The thus obtained composition for a photopolymerization type dental restorative material is polymerized by the irradiation of active rays such as ultraviolet or visible rays. The light sources used, for instance, include a variety of mercury lamps such as ultra-high, high, intermediate and low pressure ones, chemical lamps, carbon arc lamps, metal halide lamps, fluorescent amps, tungsten lamps, xenon lamps and argon ion lasers.

Additionally, the present composition may contain slight amounts of UV absorbers colorants, polymerization and other additives.

EXAMPLES

In what follows, the present invention will now be explained more specifically but not exclusively with reference to some examples and comparative examples, in which the following methacrylate or acrylate monomers having at least one unsaturated double bond were used.

Di-2-methacryloxyethyl-2,2,4-trimethylhexamethylene dicarbamate—hereinafter UDMA for short;

Triethylene glycol dimethacrylate—hereinafter 3G for short;

2,2-bis[4-(2-hydroxy-3-methacryloxypropoxy)-phenyl]propane—hereinafter bis-GMA for short;

1,3-butanediol dimethacrylate—hereinafter 1,3-BG for short;

2,2-bis(4-methacryloxypolyethoxyphenyl)-propane—hereinafter Bis-MPEPP for short; and Triethylene glycol trimethacrylate—hereinafter TMPT for short.

As the organic/inorganic composite fillers, use was made of:

A—a mixture of 20% by weight of a mixed solution off UDMA and 3G at a 5:5 ratio and 1% by weight of azobisisobutyronitrile, 50% by weight of quartz glass powders (with a maximum particle diameter of 1.5 μm and a mean particle diameter of 0.5 μm) and 30% by weight of barium glass powders (with a maximum particle diameter of 5 μm and a mean particle diameter of 1 μm) was thermally cured and pulverized at a mean particle diameter of 10 μm.

B—a mixture of 20% by weight of a mixed solution of UDMA and 3G at a 5:5 ratio and 1% by weight of azobisisobutyronitrile, 50% by weight of quartz glass powders (with a maximum particle diameter of 1.5 μm and a mean particle diameter of 0.5 μm) and 30% by weight of barium glass powders (with a maximum particle diameter of 1.5 μm and a mean particle diameter of 0.5 μm) was thermally cured and pulverized at a mean particle diameter of 10 μm.

C—a mixture of a mixed solution containing 20% by weight of TMPT and 1% by weight of azoisobutyronitrile, 50% by weight of quartz glass powders (with a maximum particle diameter of 1.5 μm and a mean particle diameter of 0.5 μm) and 30% by weight of barium glass powders (with a maximum particle diameter of 5 μm and a mean particle diameter of 1 μm) was thermally cured and pulverized at a mean particle diameter of 15 μm.

D—a mixture of a mixed solution containing 20% by weight of Bis-MPEPP and 1% by weight of azoisobutyronitrile, 50% by weight of quartz glass powders (with a maximum particle diameter of 1.5 μm and a mean particle diameter of 0.5 μm) and 30% by weight of barium glass powders (with a maximum particle diameter of 5 μm and a mean particle diameter of 1 μm) was thermally cured and pulverized at a mean particle diameter of 8 μm.

The following glass powders were used.

A—quartz glass powders having a mean particle diameter of 0.5 μm and a maximum particle diameter of 1.5 μm;

B—barium glass powders having a mean particle diameter of 1 μm and a maximum particle diameter of 5 μm; and C—barium glass powders having a mean particle diameter of 0.5 μm and a maximum particle diameter of 1.5 μm.

The fine filler used was colloidal silica (Aerosil R-972 made by Nippon Aerosil K.K.).

EXAMPLE 1

Using a kneader in a dark room, 20% by weight of Bis-MPEPP (the photopolymerization initiator used to this end was prepared by dissolving 0.5 parts by weight of a photosensitizer camphor quinone and 1 part by weight of a reducer dimethylaminoethyl methacrylate in 100 parts by weight of the monomer solution), 60% by weight of the composite filler D, 15% by weight of glass powders B and 5% by weight of a filler colloidal silica were kneaded together to obtain a paste. This restorative material was tested as follows.

Bending Strength Test

A test sample was pressed against a 2 mm×2 mm×25 mm mold with a glass plate through cellophane, and was then irradiated from above with a visible light irradiator (GC Light VL-1 made by GC Corporation) for 60 seconds all over the surface. After immersed in water for 24 hours, the sample was subject to a three-point bending test at a span of 20 mm and a crosshead speed of 1 mm/min. with an autograph (made by Shimadzu Corporation).

Ten-Point Average Roughness

A test sample was pressed against a mold of 20 mm in an inner diameter and 2 mm in thickness with a glass plate through cellophane, and was then irradiated from above with a visible light irradiator (GC Light VL-1 made by GC Corporation) for 60 seconds all over the surface. Just thereafter, the sample was polished on the thus irradiated surface with emery paper #600, and then finish-polished by Ever Light (made by GC Corporation), The surface roughness of the finish-polished side of the sample was measured with a surface roughness meter (made by Kosaka Kenkyusho) to measure its 10-point surface roughness.

Roentgenographic Properties

Testing was done according to ISO 4049-1978.

Fitness

1. A cavity with a round bevel, 2 mm in depth and 3 mm in diameter, was formed in a removed bovin tooth.

2. With a dental adhesive TRIPTON (made by I.C.I.), a test restorative material sample was filled in that cavity for curing.

3. After curing, the sample was held in water of 37° C. for 24 hours, followed by 2000-cycle thermal testing; the sample as immersed in an aqueous solution of basic fuchsin at a 30-second interval at 4° C. to 60° C.

4. After testing, the cavity was cut at its center vertically with respect to the tooth axis, and was then smooth-finished with emery paper No. 1000 while pouring water.

5. The estimation of fitness was made by to what degree the fuchsin invaded between the resin and the tooth according to the following four ranks:
a: excellent fitness with no fuchsin invasion;
b: the fuchsin invaded slightly the enamel;
c: the fuchsin reached the dentin; and
d: the fuchsin reached the lower port ion of the cavity.

Set out in Table 1 are the components and amounts used.

initiator in the monomer followed Example 1, and this was true of the comparative examples as well.

COMPARATIVE EXAMPLE 1

Quartz glass powder-containing restorative material generally said to be of the conventional type was tested.

The glass powders used were D having a maximum particle diameter of 50 μm and a mean particle diameter of 20 μm. The same tests were done with the components and amounts shown in Table 2 according to Example 1. The results are shown in Table 2, from which it is understood that good fitness was achieved, but other properties were inferior to those of the present examples.

EXAMPLES 2~10 restorative material samples were prepared by following Example 1 with the components and amounts set out in Table 1 for the same tests. The results are reported in Table 1. Note that the photopolymerization

TABLE 1

| | Compositions | | | | Physical Properties of Restorative Material | | | |
|---|---|---|---|---|---|---|---|---|
| | Methacrylate or acrylate monomer having at least one unsaturated double bond (weight/%) | Organic/ inorganic composite filler (weight/%) | Glass powder (weight/%) | Fine particle filler (weight/%) | Bending strength (kgf/cm$^2$) | Ten-point average roughness (μm) | Roentgenographic properties | Fitness |
| Example 1 | Bis-MPEPP 20 | D 60 | B 15 | Colloidal 5 silica | 1304 | 0.74 | ○ | a |
| Example 2 | Bis-MPEPP 21 | D 70 | B 5 | Colloidal 4 silica | 1456 | 0.70 | ○ | a |
| Example 3 | UDMA 10 3G 10 | A 55 | C 20 | Colloidal 5 silica | 1325 | 0.80 | ○ | a |
| Example 4 | Bis-MPEPP 25 | D 65 | C 5 | Colloidal 5 silica | 1469 | 0.63 | ○ | a |
| Example 5 | Bis-GMA 5 1,2BG 10 | C 30 | A 33 C 20 | Colloidal 2 silica | 1582 | 0.56 | ○ | a |
| Example 6 | UDMA 10 3G 10 | A 60 | A 10 B 5 | Colloidal 5 silica | 1589 | 0.68 | ○ | a |
| Example 7 | Bis-GMA 5 3G 10 | D 50 | A 20 C 12 | Colloidal 3 silica | 1354 | 0.56 | ○ | a |
| Example 8 | Bis-GMA 10 3G 5 1,3BG 5 | A 20 B 10 C 10 | A 5 B 15 C 15 | Colloidal 5 silica | 1511 | 0.71 | ○ | a |
| Example 9 | UDMA 10 3G 10 | A 20 | C 55 | colloidal 5 silica | 1399 | 0.79 | ○ | a |
| Example 10 | UDMA 10 3G 5 | B 75 | C 5 | Colloidal 5 silica | 1256 | 0.40 | ○ | a |

TABLE 2

| | Compositions | | | | Physical Properties of Restorative Material | | | |
|---|---|---|---|---|---|---|---|---|
| | Methacrylate or acrylate monomer having at least one unsaturated double bond (weight/%) | Organic/ inorganic composite filler (weight/%) | Glass powder (weight/%) | Fine particle filler (weight/%) | Bending strength (kgf/cm$^2$) | Ten-point average roughness (μm) | Roentgenographic properties | Fitness |
| Comparative Example 1 | Bis-GMA 10 3G 5 | — | D 80 | Colloidal 5 silica | 1104 | 3.24 | X | a |
| Comparative Example 2 | Bis-MPEPP 70 | — | — | colloidal 30 silica | 550 | 0.40 | X | d |
| Comparative Example 3 | UDMA 10 3G 10 | E 75 | — | colloidal 5 silica | 756 | 0.86 | X | c |
| Comparatve Example 4 | Bis-MPEPP 27 | — | C 68 | Colloidal 5 silica | 1369 | 0.89 | ○ | c |
| Comparative Example 5 | Bis-GMA 15 3G 15 | A 10 | B 55 | Colloidal 5 silica | 1214 | 0.83 | ○ | c |
| Comparative Example 6 | UDMA 15 3G 10 | A 5 | C 65 | colloidal 5 silica | 1431 | 0.76 | ○ | c |
| Comparative Example 7 | Bis-GMA 5 3G 10 | E 50 | B 32 | Colloidal 3 silica | 1354 | 0.56 | ○ | c |
| Comparative Example 8 | UDMA 12.5 3G 12.5 | F 50 | C 20 | Colloidal 5 silica | 1300 | 1.80 | ○ | a |
| Comparative Example 9 | Bis-MPEPP 21 | A 70 | E 5 | Colloidal 4 silica | 1356 | 1.70 | ○ | a |
| Comparative Example 10 | UDMA 10 3G 10 | G 60 | A 13 B 2 | colloidal 5 silica | 1523 | 0.62 | X | a |

COMPARATIVE EXAMPLE 2

Using fine filler alone in the amount shown in Table 2, similar tests were done following Example 1. The results are given in Table 2. Surface smoothness was favorable, but other properties were unfavorable.

COMPARATIVE EXAMPLE 3

Using a restorative material containing a conventional inorganic/organic composite filler, the composition and amount of which are specified in Table 2, similar tests were performed following Example 1. The organic/inorganic composite filler E having a mean particle size of 10 μm was prepared by kneading colloidal silica and TMPT at a 30:70 weight ratio and then thermally curing and pulverizing the mixture. The results are set out in Table 2. Surface smoothness was favorable but other physical properties were unfavorable.

COMPARATIVE EXAMPLE 4

In the instant example, use was made of a recently developed restorative material containing a filler made up of glass powders having a maximum particle diameter of 2 μm or less. With this restorative material the composition and amount of which are referred to in Table 2, similar tests were done following Example 1. As will be appreciated from Table 2, fitness was unfavorable.

COMPARATIVE EXAMPLES 5~7

With some restorative materials in which the amounts of the components departed from the scopes defined in the present invention, as shown in Table 2, similar tests were conducted following Example 1.

COMPARATIVE EXAMPLE 8

In the instant example, the organic/inorganic composite filler F was prepared by substituting the barium glass powders of the organic/inorganic composite filler A (with a mean particle diameter of 1 μm and a maximum particle diameter of 1.5 μm) by barium glass powders having a mean particle diameter of 7 μm and a maximum diameter of 15 μm. With the restorative material the composition and amount of which are referred to in Table 2, similar tests were conducted following the Examples. The results are set out in Table 2. Unfavorable surface smoothness was obtained.

COMPARATIVE EXAMPLE 9

Glass powder E were prepared from barium glass powders having a maximum particle diameter of 15 μm and a mean particle diameter of 7 μm. With the restorative material the composition and amount referred to in Table 2, similar tests were conducted following the Examples. The results are set forth in Table 2. Unfavorable surface smoothness was obtained.

COMPARATIVE EXAMPLE 10

In the instant example, an organic/inorganic composite filler G was used, in which the amounts of the quartz and barium glass powders used in the organic/inorganic composite filler A were changed to 70% by weight and 10% by weight, respectively. With the restorative material the composition and amount of which are referred to in Table 2, similar tests were conducted following Example 1. The results were set out in Table 2. This restorative material was unsatisfactory in terms of roentgenographic properties.

As explained above, the present invention provides a composition for dental restorative material comprising a novel combination of an organic/inorganic composite filler, glass powders and a fine filler, which is as excellent in surface smoothness as natural teeth, is less shrinkable by polymerization so that no gap can occur between the tooth and the restorative material, is improved in terms of physical properties and has roentgenographic properties; these characteristics have not been achieved with conventional compositions.

What is claimed is:

1. A composition for dental restorative material comprising:
   (a) a first methacrylate or acrylate monomer having at least one unsaturated double bond,
   (b)
     (i) a composite filler obtained by curing and pulverizing a mixture of a first glass powder component having a maximum particle diameter of 10 μm or less and a mean particle diameter of 0.1 to 5 μm with a second methacrylate or acrylate monomer having at least one unsaturated double bond,
     (ii) a second glass powder component having a maximum particle diameter of 10 μm or less and a mean particle diameter of 0.1 to 5 μm, and
     (iii) a fine-particle filler having a mean particle diameter of 0.01 to 0.04 μm, and
   (c) a photopolymerization initiator.

2. A composition as claimed in claim 1, which contains 20% by weight or more of the first and second glass powder component having roentgenographic properties on the basis of the total weight of the first and second glass powder components.

3. A composition as claimed in claim 1 or 2, wherein said second methacrylate or acrylate monomer having at least one unsaturated double bond is the same as said first methacrylate or acrylate monomer (a) having at least one unsaturated double bond.

4. A composition as claimed in any one of claims 1 or 2, wherein said organic/inorganic composite filler (b-i) has a mean particle diameter of 5 to 50 μm.

5. A composition as claimed in any one of claims 1 or 2, wherein the amount of said methacrylate or acrylate monomer (a) having at least one unsaturated double bond lies in the range of 5 to 30% by weight on the basis of the total weight of said composition.

6. A composition as claimed in any one of claims 1 or 2, wherein the amount of said organic/inorganic composite filler (b-i) lies in the range of 20+o 80% by weight on the basis of the total weight of said composition.

7. A composition as claimed in any one of claims 1 or 2, wherein the amount of the first glass powder component of said composite filler (b-i) lies in the range of 60 to 90% by weight on the basis of the total weight of said composition.

8. A composition as claimed in any one of claims 1 or 2, wherein the amount of said glass powder component (b-ii) lies in the range of 5 to 60% by weight on the basis of the total weight of said composition.

9. A composition as claimed in any one of claims 1 or 2, wherein the amount of said fine-particle filler (b-iii) lies in the range of 1 to 8% by weight on the basis of the total weight of said composition.

10. A composition as claimed in any one of claims 1 or 2, wherein the first glass powder component of said composite filler (b-i) and said second glass powder component (b-ii) have a maximum particle diameter of 5 μm or less and a means particle diameter of 0.1 to 2 μm.

* * * * *